United States Patent [19]
Schiraldi et al.

[11] Patent Number: 6,103,919
[45] Date of Patent: Aug. 15, 2000

[54] CATALYTIC SYSTEM AND METHOD FOR COUPLING OF AROMATIC COMPOUNDS

[75] Inventors: David Anthony Schiraldi, Charlotte, N.C.; Sheldon Christopher Sherman, Alpharetta, Ga.; Dhiraj Sudesh Sood, Baton Rouge, La.; Mark Gilmore White, Woodstock, Ga.

[73] Assignee: Arteva North America S.A.R.L., Zurich, Switzerland

[21] Appl. No.: 09/111,487

[22] Filed: Jul. 7, 1998

[51] Int. Cl.[7] ............................. C07F 15/00; C07C 67/00; B01J 31/00
[52] U.S. Cl. ........................... 556/136; 502/170; 502/171; 562/480; 585/427; 560/96
[58] Field of Search ...................... 502/170, 171; 556/136; 585/427; 562/480; 560/96

[56] References Cited

U.S. PATENT DOCUMENTS

| | | | |
|---|---|---|---|
| 3,895,055 | 7/1975 | Itatani et al. | 260/479 R |
| 3,963,787 | 6/1976 | Ichikawa et al. | 260/613 R |
| 4,008,266 | 2/1977 | Intille | 260/475 R |
| 4,164,518 | 8/1979 | Ichikawa et al. | 585/427 |
| 4,294,976 | 10/1981 | Itatani et al. | 560/76 |
| 5,175,244 | 12/1992 | Budzelaar et al. | 528/392 |

FOREIGN PATENT DOCUMENTS

| | | |
|---|---|---|
| 0 360 359 | 3/1990 | European Pat. Off. |
| 0 390 292 | 10/1990 | European Pat. Off. |

OTHER PUBLICATIONS

R. Van Helden & G. Verberg, "The Oxidative Coupling of Aromatic Compounds with Palladium Salts", Rev Triv. chim., 1965, 84, 1263.

Ferrers R.S. Clark et al, Reactions of Palladium (II) with Organic Compounds., J. Chem. Soc., Perkins I, 1974, 1289.

J.M. Davidson et al, "Reaction of Metal Ion Complexes with Hydrocarbons", J. Chem Soc. (A), 1968, 1324.

J.M. Davidson et al. "Reactions of Palladium Complexes with Benzene and Toluene", Chemistry and Industry, Mar. 12, 1966, 457.

Y. Taniguchi et al., "Palladium (II) Catalyzed Carboxylation of Aromatic Compounds with CO under Very Mild Conditions", Chemistry Letters, 1995, 345.

B. Cornils & W.A. Herrmann, "Applied Homogeneous Catalysis with Organometallic Compounds", 1996, VCH.

*Primary Examiner*—Porfirio Nazario-Gonzalez
*Attorney, Agent, or Firm*—Gregory N. Clements

[57] ABSTRACT

A catalytic process for production of biphenyl and its derivatives by coupling of substituted or unsubstituted monoaryl compounds in the presence of a catalytic system comprising at least one Pd (II) compound and a strong acid or a mixture of acids. The process provides high conversions and high selectivity under mild temperature conditions and short reaction times. The strong acid or mixture of acids has a Hammett acidity of less than about −10, and contains a predominant amount of counterions which form a weak ligand complex with palladium (II). The method is highly selective to formation of desired biaryl isomers, such as 4,4'-isomers, and allows control of the relative amounts of isomers of biaryl compounds and substituted monoaryl compounds in the final product.

79 Claims, No Drawings

CATALYTIC SYSTEM AND METHOD FOR COUPLING OF AROMATIC COMPOUNDS

FIELD OF THE INVENTION

This invention relates to a method for producing biaryl compounds by coupling monoaryl compounds in the presence of a catalytic system obtained by admixing of a Pd (II) compound and a strong acid or mixture of strong acids. The invention is also related to a catalytic system for coupling of substituted or unsubstituted aryl compounds.

BACKGROUND OF THE INVENTION

Biaryl compounds such as biphenyl, dimethyl biphenyl, and other various substituted biphenyl derivatives can be functionalized and converted to monomers for production of various high performance polymeric compounds such as polyesters or polyamides. Various biaryl compounds can be obtained by homocoupling of the same or heterocoupling of different monoaryl compounds. Coupling of monoaryls is an efficient technique for production of a variety of biaryls because monoaryls are readily available and inexpensive starting materials.

Coupling of aryl halides is one of the known methods for production of biaryls. This method is disclosed, for example, in "Applied Homogeneous Catalysis with Organometallic Compounds", Vol.2, B. Cornis and W. A. Herman, 1996, VCH, and is known as the Heck reaction. While effective in production of biaryls, this method suffers from the need for costly purification processes and recycling of its side products, i.e., metal halides.

Another method, also disclosed in the Cornis reference and known as the Suzuki reaction, is the coupling of aryl boron. This method, however, includes the strenuous step of preparation of boron intermediates. As with the aryl halide coupling, this method also suffers from costly recycling and disposal problems.

R. Van Helden et al., Rec. Triv. chini., 1965, 84,1263 reported oxidative coupling of benzene and substituted benzenes using palladium chloride and sodium acetate in acetic acid solution. The reported reaction took place at high temperatures and metallic palladium is precipitated in the reaction system.

In the Van Helden et al. process the palladium compound is a reactant rather than a catalyst. As such, it is used in these processes in stoichiometric amounts in the dimerization reaction. Since palladium is a very rare metal and its compounds are extremely expensive, use of palladium compounds in stoichiometric amounts, rather than catalytic amounts, makes these processes commercially impractical and the final products expensive.

U.S. Pat. No. 4,008,266 to Intille discloses coupling of monoaryl compounds in the presence of a mercuric oxyanion and a Pd (II) compound. The reaction takes place at elevated temperatures and high pressures. A minimum oxygen pressure of 200 psi is required in order for the coupling reaction to proceed as a catalytic reaction.

Oxidative coupling of monoaryls in the presence of Pd (II) catalysts and trifluoroacetic acid, with or without addition of Cu (II) co-catalysts, is reported in *J. Chem. Soc., Perkin I*, 1974, 1289. However, the reaction time, which may be up to 14 days, is too long for large scale, commercially feasible production. Moreover, the reaction product contains a mixture of biaryl isomers such as 3,3'-, 3,4'- or 4,4'-isomers, and a high amount of di-aromatic compounds.

Coupling of monoaryl compounds using catalytic amounts of palladium (II) acetate is disclosed in U.S. Pat. Nos. 3,895,055 to Itatani et al. and 4,294,976 to Itatani et al. While this technique uses only catalytic amounts of palladium (II) compounds when air is used as an oxidant, the reaction takes place at elevated temperatures of about 150° C. and an oxygen partial pressure of at least 5 kg/cm$^2$. For example, while the toluene coupling rate at 150° C. and air pressure (50% oxygen) of 750 psi is about 18.5 mmol/hour, the estimated toluene coupling rate at room temperature is only about 0.046 mmol/hour based on activation energy data for this reaction.

The coupling of monoaryl compounds in the presence of a Pd (II) acetate catalyst is disclosed in U.S. Pat. Nos. 3,963,787 and 4,164,518, both to Ichikawa et al. An increase of catalytic activity is reported for use of organic carboxylates, halogen, and oxyhalogen compounds of zirconium in conjunction with the palladium (II) catalyst. To achieve any considerable yield of biaryl compounds, the reaction takes place at high temperatures of 100° C. and above and at high oxygen pressure.

The present invention provides a catalytic system obtained by admixing a palladium (II) compound and a strong acid or mixture of acids for coupling of monoaryl compounds. The method of coupling monoaryl compounds in the presence of catalytic amounts of the catalytic system may be used to selectively produce isomers, such as 4,4'-isomers, for the production of desired polymers. The reaction conditions can be easily adjusted to yield different isomers of biaryl compounds in different proportions, and the reactions proceed to high yields at room temperatures within relatively short reaction times.

SUMMARY OF THE INVENTION

The coupling of at least one monoaryl compound to produce biaryl compounds in high yields with high selectivity may be achieved with a catalytic system comprising a palladium (II) compound and at least one acid having a Hammett acidity of less than about $-10$, preferably less than $-14$. The catalytic system may be obtained by admixing a palladium (II) compound and a strong acid or mixture of acids wherein the acid or the mixture of acids has a Hammett acidity of less than about $-10$, preferably less than $-14$, and contains a predominant or catalytically effective amount of counterions that form weak ligand complexes with the Pd (II) ion. Hammett Acidity, HI, is defined as $H_o = pK_{BH+} - \log(C_{BH+}/C_B)$; where $K_{BH+}$ is the ionization constant for the indicator, $C_{BH+}$ is the concentration of the protonated indicator and $C_B$ is the concentration of the unprotonated indicator. (Ref.: Van Norstrand's Scientific Encylcopedia, 5th Ed.)

The biaryl compounds may be produced by coupling of substituted or unsubstituted monoaryl compounds in the presence of a catalytic amount of the catalyst system. According to the method of the present invention monoaryl compounds of the formula (I):

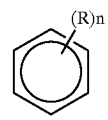

(I)

wherein R is the same or different and is alkyl, alkoxy, aryloxy, hydroxy, amino, carboxyl, nitro, nitroso, cyano, amido, hydroxyamino, carboxylic ester, ether, sulfo, sulfate or another functional group, and n is an integer from 0 to 5, are coupled, or dimerized, in the presence of a catalytic amount of at least one palladium (II) compound and at least one strong acid with a Hammett acidity of less than −10, and contain a predominant amount of counterions that will form weak ligand complexes with Pd (II), such as triflic acid, to produce biaryl compounds of the formula (II):

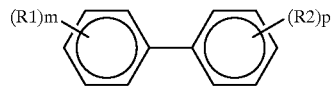
(II)

wherein both m and p are integers from 0 to 5, m and p can be the same or different, and m and p correspond to the respective n's in the starting compounds represented by formula (I), and wherein each one of R1 and R2 can be the same or different and correspond to the R's in the starting compounds represented by formula (I).

The processes according to the present invention may be advantageously conducted at low temperatures and pressures in short periods of time, for example, at room temperature for about 2–4 hours. In embodiments of the present invention reaction temperatures and times may range from about −78° C. to about 200° C., for example from about −20° C. to about 150° C. for about from 0.1 hour to about 5 hours. Reaction pressures may range from atmospheric pressure of about 14 psia to about 2000 psia. The process of coupling monoaryl compounds to produce biaryl compounds corresponding to formula (II) can be conducted for selective production of a desired isomer, such as a 4,4'-isomer, by varying reaction conditions and relative amounts of the reactants.

DETAILED DESCRIPTION OF THE INVENTION

A process for production of biaryl compounds in accordance with the present invention allows for controlled production of biaryls with a desired isomer distribution under mild conditions. The process is economical and does not suffer from production of side-products which are difficult to dispose of or recover. Biaryl compounds are obtained by monoaryl coupling or dimerization in the presence of a catalytic amount of at least one palladium (II) compound and in the presence of a least one strong or super acid. The biaryl compounds may be produced without the need for a halogenated monoaryl reactant and without elimination of halogen compounds.

Monoaryl compounds, useful as reactants in the process of the invention include a wide variety of monoaromatic compounds. Exemplary monoaromatic compounds are represented by the general formula (I):

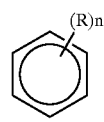
(I)

wherein n is an integer from 0 to 5, and

R is the same or different and is alkyl, alkoxy, aryloxy, hydroxy, amino, carboxyl, nitro, nitroso, cyano, amido, hydroxyamino, carboxylic ester, ether, sulfo, sulfate, or another functional group.

Any substituted aryl compound, except for fully substituted aryls can be coupled employing the process of the present invention.

In the above formula (I), exemplary alkyl groups for R are linear or branched alkyls having one to six carbon atoms; for example, methyl, ethyl, propyl, isopropyl, butyl, isobutyl, sec-butyl, tert-butyl, pentyl, isopentyl, neopentyl, tert-pentyl, hexyl and dimethylbutyl.

Examples of alkoxy groups for R are those wherein at least one hydroxyl group is substituted on a linear or branched alkyl having one to four carbon atoms; for example, as methyl, ethyl, propyl, isopropyl, butyl, isobutyl, sec-butyl and tert-butyl.

Examples of monoaryl compounds represented by the formula (I) are benzene, toluene, dimethylbenzene, trimethylbenzene, ethylbenzene, isopropylbenzene, xylenes, diethylbenzenes, diisopropylbenzenes, benzoic acid, methyl benzoate, benzonitrile, benzophenone, nitrobenzene, nitrotoluene, anisole, ethoxybenzene, diethoxybenzenes, ethoxytoluene, phenol, phenyl acetate, phenyl hexanoate, and others. Biaryl compounds that may be obtained by cross-coupling of monoaryl compounds, i.e. by coupling of two or more different monoaryls are within the scope of this invention.

In preferred embodiments n is an integer from 0 to 2, and R is a lower alkyl group, for example, a $C_1$ to $C_4$ alkyl group, a carboxylic acid group, or a carboxylic ester group. Most preferably the monoaryl compound is toluene, benzoic acid or methyl benzoate.

Examples of the resulting biaryl compounds which may be produced in accordance with the present invention are represented by the general formula (II):

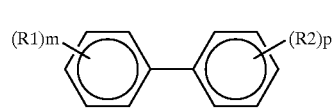
(II)

wherein both m and p are integers from 0 to 5, m and p can be the same or different, and m and p correspond to the respective n's in the starting compounds represented by formula (I), and wherein each one of R1 and R2 can be the same or different and correspond to the R's in the starting compounds represented by formula (I).

In the case of homocoupling of monoaryl compounds, m=p and each R1 corresponds to an identical R2. In the case of heterocoupling of different monoaryl compounds there will be either no exact correspondence of R1's to R2's or m will be different from p.

R can also be a halogen, such as chlorine or bromine. However, halogenated monoaromatic compounds are less preferred since the coupling reaction of halogenated aryls may occur with liberation of the halogen and may result in formation of halogenated side products.

The catalyst system that is used in the invention and which allows for conversion of monoaryl compounds to biaryl compounds at relatively mild conditions is a combination of a strong acid or a mixture of acids with:

(a) a palladium (II) compound, or (b) reaction products or a complex of the palladium (II) compound with the strong acid or the mixture of acids, or (c) mixtures of the palladium (II) compound and the reaction products or a complex of the palladium (II) compound and the strong acid or the mixtures of acids. The catalytic system is obtained by admixing predetermined amounts of one or more palladium (II) compounds with a strong acid of a mixture of acids. It is preferred that the catalyst system is obtained by admixing or a palladium (II) compound with at least equimolar or excess amounts of the strong acid or the mixture of acids.

Exemplary palladium (II) compounds which may be employed are palladium triflate, palladium acetate, palladium acetylacetonate and mixtures thereof The preferred palladium (II) compound is palladium triflate. It may be obtained by contacting wet palladium nitrate or palladium acetate with an excess of triflic acid, followed by evaporation of the liquid from the reaction mixture. Palladium triflate can also be obtained in situ by addition of triflic acid and a palladium compound such as, but not limited to, palladium acetate or palladium acetylacetonate to the aryl substrate. However, formation of palladium triflate in situ from the above-mentioned palladium (II) compounds, rather than adding the compound palladium triflate to the reactants, is less preferred. It has been found to result in lowered production of coupled aromatic or bi-aromatic compounds and increased production of higher-substituted aromatic compounds. For example, if a monosubstituted aromatic compound such as toluene is used as a substrate, a di-substituted aromatic compound such as methyl acetophenone may be produced in higher amounts.

The catalytic amount of palladium (II) compound added to or used in the reaction mixture may be from about 0.001 mole to about 0.1 mole per mole of monoaryl compound. For coupling of monoaromatic compounds such as benzene or toluene, the preferred amount of palladium (II) compound is from about 0.01 mole to about 0.08 mole, most preferably from about 0.015 mole to about 0.04 mole per mole of the monoaryl reactant. For monoaromatic compounds such as methyl benzoate or benzoic acid the preferred amount of palladium (II) compound is from about 0.0012 mole to about 0.02 mole per mole of monoaryl compound. If less than 0.001 mole of palladium compound is used then the yield of the final product becomes low. Use of higher than 0.1 mole of the palladium compound, while increasing the yield of biaryl compounds, becomes economically undesirable due to the high cost of palladium and its compounds.

In embodiments of the invention the molar ratio of the palladium II compound to the strong acid or mixture of acids may range from about 0.0003:1 to about 10:1, preferably from about 0.005:1 to about 5:1. The molar ratio employed may vary depending on the monoaryl compound used for the coupling reaction. For example, for benzene or a alkyl substituted benzene such as toluene, the molar ratio may range from about 0.003:1 to about 1:1, preferably from about 0.007:1 to about 0.27:1, most preferably from about 0.018:1 to about 0.09:1. For methyl benzoate or benzoic acid the ratio may preferably be from about 0.08:1 to about 5:1, most preferably from about 0.1:1 to about 2:1. If the ratio of the amount of palladium compound to the amount of strong acid or the mixture of acids is higher than 10:1, the conversion rates tend to be too low. If the ratio is lower than 0.0003, then the selectivity of the reaction towards production of 4,4' isomers in the case of coupling monosubstituted benzenes tends to be low.

Any strong acid or superacid with a Hammett acidity of lower than about −10 and which contains a predominant or catalytically effective amount of counterions that form weak ligand complexes with Pd (I) ion or its compounds may be employed in the present invention. Mixtures of acids that have a Hammett acidity of less than about −10 and contain a predominant amount of counterions that form weak ligand complexes with Pd (II) may also be used in the present invention. Examples of such counterions include, but are not limited to triflate, trifluoroacetate, fluorosulfonate, acetate, acetyl acetonate, bis(trifluoromethylsulfonyl)imide, perfluorotetraphenyl borate, and tetrakis[3,5-bis(trifluoromethyl) phenyl]borate. Examples of counterions that form strong Pd (II) complexes, and therefore are generally not effective in the catalytic system of the present invention include sulfate, chloride, and nitrate. Generally, counterions of organic acids are known to form good leaving groups, i.e., they form a weak complex with palladium (II), while counterions of inorganic acids form poor leaving groups, i.e. form a strong complex with palladium (II).

Thus, counterions of the acid employed for the invention are counterions that do not strongly chelate palladium (II) ion or its compounds. The presence of any counterion that forms a strong complex with palladium (II) or strongly chelates a palladium (II) compound may be tolerated, but is not desirable. By forming a strong complex with palladium (II), such counterions will effectively remove that amount of palladium (II) that is involved in the formation of a strong complex from the catalytic process.

Examples of acids with a Hammett acidity lower than −10 and which are suitable for the catalytic system of the present invention are triflic acid, fluorosulfonic acid, 1:1 to 1:0.15 mixtures of antimony pentafluoride and hydrofluoric acid, and 1:0.2 mixtures of fluorosulfonic acid with either antimony or tantalum pentafluorides. Solid acids such as sulfated zirconia or sulfated titania may also be employed in the invention. Triflic acid has a Hammett acidity of less than −14 and is the preferred acid for use in the present invention. Various mixtures of acids, including aqueous mixtures, may also be used in the present invention as long as the Hammett acidity of the mixture is less than −10 and the mixture comprises a predominant or catalytic amount of counterions that do not form a strong complex with the palladium (II) ion or palladium (II) compound. For example, a mixture of triflic with trifluorosulfonic acid can be used in combination with a palladium (II) compound as a catalytic system according to the present invention. The amount of triflic acid in the mixture with trifluoroacetic acid can be as high as 99% by weight and must be at least about 5% by weight in order for the mixture to have a Hammett acidity of less than about −10.

The amount of strong acid or mixture of acids added to or used in the reaction mixture may be between about 0.005 mole and about 3 moles per 1 mole of the monoaryl compound. The amount of acid or the mixture of acids may depend upon the monoaromatic compound that is coupled using the catalytic system according to the present invention. For coupling of monoaromatic compounds that do not undergo side ion-co-catalyzed reactions, such as benzene or alkyl substituted benzenes such as toluene, large amounts of acids can be tolerated and may even be beneficial.

The preferred amounts of the strong acid or the mixture of acids is from about 0.25 mole to about 2 moles, most preferably from about 0.45 mole to about 1.1 moles per mole of monoaromatic compound. However, in coupling reactions of monoaromatic compounds that easily undergo side reactions catalyzed by acids, such as monoaryl compounds that contain one or more amino, alkyl-substituted amino, hydroxy, aldo, keto, ester, carboxy, sulfo, cyano, imino, or nitroso groups, much smaller amounts of the strong acid or the mixture of acids may be used. Exemplary of such compounds are mono aromatic amines, alcohols, aldehydes, ketones, esters, carboxylic acids, sulfonic acids, nitriles, or imiines, such as methyl benzoate or benzoic acid. In such cases, the amount of the acid or mixtures of acids may be from about 0.01 to about 0.05 mole of the strong acid or the mixture of acids per mole of monoaromatic compound.

While the process can be conducted in the presence of small catalytic amounts of the acid or large amounts of acid, the selectivity towards production of desirable 4,4'-isomers from monosubstituted aryl compounds decreases as the amount of the acid present increases. Also a large excess of strong acid may present a problem of handling the acid, and tends to make the process less practical.

Generally, during coupling of monoaryl compounds products of different structure can be obtained. There are two different types of coupling: (1) nuclear to nuclear coupling that results in production of biaryl compounds of the formula (II), and (2) nucleus-to-side chain coupling that results in production of di-aryl compounds of the following formula (III):

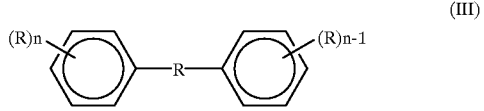

wherein R and n are defined as above for formula (I).

During either type of coupling, various isomers can be obtained. Not only does the process of the invention result in minimum formation of di-aryl compounds of formula (III), the process further allows for control of the isomeric structure of the biaryl final product. For example, in homo- or hetero coupling of mono substituted aryl compounds, it is possible to control the production of the relative amounts of 4,4'-, 3,3'- or 3,4'-isomers in the final product. The relative amounts of the isomers may be adjusted by adjusting the reaction conditions or the relative amounts of the reactants in the reaction mixture. Thus, during coupling of monosubstituted aryl compounds such as toluene, benzoic acid, or methyl benzoate, the process of the invention allows for maximum production of the desirable 4,4'-isomer. 4,4'-isomers which may be produced in accordance with the present invention are of the formula (IV):

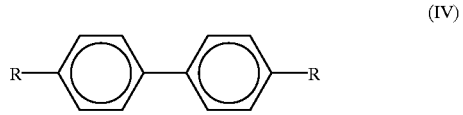

wherein R is defined as above and is preferably R', where R' is an alkyl, carboxyl or carboxylic ester group. A 4,4'-isomer, such as 4,4'-dimethyl biphenyl, is the most desirable isomer out of all possible biphenyl isomers because it can be functionalized and used in the synthesis of polyesters and polyamides, including liquid crystal polymers.

The reaction can be run at various temperatures depending on the desired isomer ratio in the final product. The reaction can be run at as low as dry ice temperature, i.e. about −78° C., or as high as about 200° C., for example in the range from about −20° C. to about 150° C., preferably from about 0° C. to about 75° C. However, very low temperatures, such as −78 ° C., are not economical for industrial application. Moreover, if the selectivity toward the production of the 4,4'-isomer is desired, the temperature should be between 0° C. and 50° C., preferably at about room temperature.

Reaction times may range from about 0.1 hour to about 5 hours, preferably from about 1 hour to about 3 hours.

The reaction may be conducted at pressures of from about atmospheric pressure, about 14 psia, to about 2000 psia, preferably at pressures less than about 1000 psia.

Not wishing to be bound to any specific theory or mechanism, it is believed that coupling of monoaryl compounds in the presence of the catalytic system according to the present invention proceeds via an aryl palladium complex.

In the case of homo- or hetero- coupling of monosubstituted aryl compounds, such mechanism would favor formation of 4,4'-biphenyl isomer. However, it has been found that the predominant product in the coupling of monosubstituted aromatic compounds such as toluene is the 3,4'-isomer. This can be explained by considerable isomerization of the 4,4'-isomer initially formed to the more thermodynamically stable 3,4'-isomer in the presence of the strong acid.

Biaryl compounds obtained by the process of the invention can be used as intermediates for production of various chemical and pharmaceutical compounds. Furthermore, biaryls obtained by the methods of the present invention can be easily functionalized by either introducing functional groups or by converting existing functional groups to desired functional groups. For example, the alkyl-substituted biaryls can be easily converted to polybasic carboxylic acids, their esters or other desired polyfunctional compounds to be used as a monomer in the synthesis of high performance polymers.

The catalytic system according to the present invention is a system obtained by admixing a palladium (II) compound with a strong acid or mixture of acids which acid or mixture of acids has a Hammett acidity of less than −10 and which contain at least a predominant amount of counterions that will form weak ligand complexes with Pd (II). This catalytic system is quite unique and can be effectively used in a variety of reactions involving electrophilic substitution of monoaryl reactants.

The present invention is further illustrated in the following examples wherein all parts, percentages, and ratios are by moles, all temperatures are in ° C., and all pressures are atmospheric or in psia unless otherwise indicated:

EXAMPLE A

Preparation of Palladium Triflate catalyst.

Palladium triflate [Pd(Tfo)$_2$] was prepared from wet palladium (II) nitrate [Pd(NO$_3$)$_2$] or palladium (II) acetate [Pd(AcO)$_2$] with excess of triflic acid [TfOH] at room temperature (typically about 18 to about 30° C.). The liquid was evaporated from the reaction mixture under vacuum at 150 ° C and dry palladium triflate was obtained and stored under inert gas for further use as a catalyst in the aryl coupling reactions.

EXAMPLE 1

0.6 g (1.48 millimoles) of palladium triflate was charged at room temperature (21° C.) into a round bottom flask equipped with a stirrer. After purging the flask with dry nitrogen for 5 min, 5.6 g (60.9 millimoles) of dry toluene was then added under nitrogen flow. The flask was placed in a bath of room temperature water and 9.7 g (64.7 millimoles) of triflic acid was added. The thus obtained mixture was placed under nitrogen at atmospheric pressure and was continuously stirred. The reaction was allowed to continue for 120 minutes. Samples of the oil phase were taken at 30, 60 and 120 minutes, and were analyzed by GS/MS. The reaction was then stopped by addition of ice to the reaction mixture. The organic phase was analyzed for yield of the dimethyl biphenyl isomers and other products. The results are shown in Table I.

EXAMPLES 2–4

The procedure of Example 1 was followed except that different molar ratios (0.47, 0.74, and 1.96 or 2.0) of triflic acid to toluene were used. The ratio of the palladium triflate to toluene was 0.02, 0.014, and 0.018, respectively. The final product was analyzed by GC/MS. The results are shown in Table I.

EXAMPLES 5–6

The procedure of Example 1 was followed except that different molar ratios (0.039 and 0.072) of palladium triflate to toluene were used. The ratio of the triflic acid to toluene was about 0.87 and 1.0, respectively. The final product was analyzed by GC/MS. The results are shown in Table I.

EXAMPLE 7

The procedure of Example 1 was followed except that palladium acetate was used instead of palladium triflate. A molar ratio of palladium acetate to toluene of about 0.027 was used. The reaction time was 270 minutes. The final product was analyzed by GC/MS. The results are shown in Table I.

COMPARATIVE EXAMPLE 1

The procedure of Example 1 was followed except that metallic palladium was used instead of palladium triflate. A molar ratio of triflic acid to toluene of about 1.17 was used. The final product was analyzed by GC/MS. The results are shown in Table I.

COMPARATIVE EXAMPLE 2

The procedure of Example 1 was followed except that no triflic acid was added to the reaction mixture. A molar ratio of palladium triflate to toluene of about 0.016 was used. The reaction was carried out for 4 hours, then the reaction temperature was raised to 60° C. and continued for an additional 40 minutes. The final product was analyzed by GC/MS. The results are shown in Table I.

COMPARATIVE EXAMPLE 3

The procedure of Example 1 was followed except that no triflic acid was added to the reaction mixture and palladium acetate was used instead of palladium triflate. A molar ratio of palladium acetate to toluene of about 0.02 was used. The final product was analyzed by GC/MS. The results are shown in Table I.

COMPARATIVE EXAMPLE 4

The procedure of Example 1 is followed except that no palladium triflate was added to the reaction mixture. A molar ratio of triflic acid to toluene of about 1.08 was used. The final product was analyzed by GC/MS. The results are shown in Table I:

TABLE I

| | Example | | | | | | |
|---|---|---|---|---|---|---|---|
| | 1 | 2 | 3 | 4 | 5 | 6 | 7 |
| Catalyst | $Pd(TfO)_2$ + TfOH | $Pd(TfO)_2$ + TfOH | $Pd(TfO)_2$ + TfOH | $Pd(TfO)_2$ + TfOH | $Pd(TfO)_2$ + TfOH | $Pd(TfO)_2$ + TfOH | Pd(AcO)TfOH |
| TfOH/Tol (molar) | 0.91 | 0.74 | 0.47 | 1.96 | 0.87 | 1.00 | 0.95 |
| Pd/Tol. (molar) | 0.020 | 0.014 | 0.02 | 0.018 | 0.039 | 0.072 | 0.027 |
| Rxn. Time/min | 120 | 120 | 120 | 120 | 120 | 120 | 270.00 |
| Pd(II)/TfOH | 0.022 | 0.028 | 0.04 | 0.009 | 0.04 | 0.072 | 0.036 |
| Conversion, % | 5.61 | 5.43 | 2.4 | 4.80 | 12.05 | 21.97 | 7.58 |
| Prod. Sel., % | | | | | | | |
| 2,2'-dmbp* | 0.62 | 0.66 | | | 0.54 | 1.04 | 0.11 |
| 2,3'-dmbp | 3.25 | 2.69 | | | 3.89 | 7.54 | 2.23 |
| 2,4'-dmbp | 2.68 | 1.98 | | | 3.72 | 8.66 | |
| 3,3'-dmbp | 5.21 | 4.59 | 11.4 | 9.9 | 3.05 | 2.75 | 2.64 |
| 3,4'-dmbp | 58.25 | 49.29 | 23.6 | 65.4 | 49.58 | 48.96 | 29.17 |
| 4,4'-dmbp | 15.76 | 19.44 | 65 | 6.8 | 23.45 | 23.09 | 14.15 |
| Total dmbps | 85.77 | 78.65 | ~99 | ~85 | 84.23 | 92.04 | 49.60 |
| Trimer | 8.87 | #5.33 | | | 14.01 | 4.88 | 12.49 |
| Methylacetophenone | 0.12 | | | | 0.17 | | 37.91 |
| Unknowns | 5.24 | 6.02 | | | 1.59 | 3.07 | tr. |

| | Comparative Example | | | |
|---|---|---|---|---|
| | 1 | 2 | 3 | 4 |
| Catalyst | Pd + TfOH | $Pd(TfO)_2$ | $Pd(AcO)_2$ | TfOH |
| TfOH/Tol. (molar) | 1.17 | 0 | 0 | 1.08 |
| Pd/Tol. (molar) | 0.040 | 0.016 | 0.02 | 0 |
| Rxn. time/min | 120 | 210 | 180 | 120 |
| Pd (II)/TfOH | 0.035 | — | 0 | |
| Conversion, % | 1.52 | 0.72 | ~0 | ~0 |
| Prod. Sel., % | | | | |
| 2,2'-dmbp | tr | 1.13 | | |
| 2,3'-dmbp | 0.86 | 6.01 | | |
| 2,4'-dmbp | 0.08 | 6.64 | | |

TABLE I-continued

| | | |
|---|---|---|
| 3,3'-dmbp | 1.14 | 0.03 |
| 3,4'-dmbp | 7.82 | 14.66 |
| 4,4'-dmbp | 2.59 | 5.05 |
| Total dmbps | 12.49 | 32.39 | no dmbps | no dmbps |
| Trimer | 86.78 | 0.28 |
| Methylacetophenone | | tr. |
| Unknowns | 0.73 | 67.33 | dmbp* = dimethyl biphenyl

As evident from the results in Table 1, neither palladium acetate alone nor triflic acid alone can effectively catalyze the toluene coupling reaction. Palladium triflate used alone resulted in very low conversion of toluene with a decreased biaryl fraction compared to the conversions and the biaryl fractions obtained with the use of both palladium triflate and triflic acid. Metallic palladium with triflic acid catalyst produced low conversion of toluene with a very low biaryl fraction compared to the conversion and biaryl fraction obtained with the use of both palladium triflate and triflic acid. Use of palladium acetate together with triflic acid, according to the method of the present invention, results in high conversion of toluene. However, compared to the use of palladium triflate and triflic acid: 1) the production of biaryl compounds is lower, and 2) the production of the substituted aromatic compound methyl acetophenone is higher. As shown in Examples 1–3 and 5–7, the fraction of 4,4'-isomer is at least about 14% on a molar basis, based upon the total weight of the reaction products.

EXAMPLE 8

3.5 millimoles of palladium acetate was charged at room temperature (21° C.) into a round bottom flask equipped with a stirrer. After purging the flask with dry nitrogen for 5 min, 210 millimoles of dry methyl benzoate was then added under nitrogen flow. The flask was placed in a water bath and heated to 65° C., then 3.5 millimoles of triflic acid was added. The thus obtained mixture was placed under nitrogen at atmospheric pressure and was continuously stirred. The reaction was allowed to continue for 240 minutes. The reaction was then stopped by addition of ice to the reaction mixture. The organic phase was analyzed by GS/MS for yield of the dimethylbibenzoic acid ester isomers and other products. The results are shown in Table II.

EXAMPLE 9

0.5 millimoles of palladium acetate was charged at room temperature (21° C.) into a stainless steel autoclave equipped with a stirrer. 331 millimoles of dry methyl benzoate was then added. Then 3.5 millimoles of triflic acid was added. The autoclave was sealed, pressurized to 750 psia with air that was enriched with oxygen such that it contained 50% $O_2$. The reaction was allowed to continue for 240 minutes. The organic phase was analyzed by GS/MS for yield of the dimethylbibenzoic aicd ester isomers and other products. The results are shown in Table II.

COMPARATIVE EXAMPLE 5

The procedure of Example 8 was followed except that the amount of added methyl benzoate was 332 millimole, amount of added palladium acetate was 0.5 millimole, and 0.5 millimole of pentanedione was added in place of triflic acid. The reaction temperature was raised to 150° C. The final product was analyzed by GC/MS. The results are shown in Table II.

COMPARATIVE EXAMPLE 6

The procedure of Example 9 was followed except that the amount of added methyl benzoate was 334 millimoles, the amount of added palladium acetate was 0.52 millimole and 0.55 millimole of pentanedione was added in place of triflic acid. The reaction temperature was raised to 28° C. The final product was analyzed by GC/MS. The results are shown in Table II.

COMPARATIVE EXAMPLE 7

The procedure of Example 9 was followed except that the amount of added methyl benzoate was 334 millimoles, amount of added palladium acetate was 0.52 millimole, and 0.48 millimole of pentanedione was added in place of triflic acid. The reaction temperature was raised to 100° C. The final product was analyzed by GC/MS. The results are shown in Table II.

COMPARATIVE EXAMPLE 8

The procedure of Example 9 was followed except that the amount of added methyl benzoate was 332 millimole, amount of added palladium acetate was 0.51 millimole, and 0.5 millimole of pentanedione was added in place of triflic acid. The reaction temperature was raised to 150° C. The final product was analyzed by GC/MS. The results are shown in Table II:

TABLE II

| | Examples | | | | | |
|---|---|---|---|---|---|---|
| | 8 | 9 | Comp. 5 | Comp. 6 | Comp. 7 | Comp. 8 |
| Methylbenzoate, mmol | 210 | 331 | 332 | 334 | 334 | 331 |
| Pd(ii)ion, mmol/counter ion | 3.51(OAc)* | .50/(OAc) | 0.50/(OAc) | 0.52/(OAc) | 0.52/(OAc) | 0.51/(OAc) |
| Ligand, mmol/description | 0 | 0 | 0.5/(Hacac)** | 0.55/(Hacac) | 0.48/(Hacac) | 0.5/(Hacac) |
| Triflic acid (TfOH), mmol | 3.5 | 3.5 | 0 | 0 | 0 | 0 |
| Pd (II)/TfOH ratio | 1 | 015 | — | — | — | — |
| Reaction time, min | 240 | 240 | 240 | 240 | 240 | 240 |
| Temperature, ° C. | 65 | 65 | 150 | 28 | 100 | 150 |

TABLE II-continued

| | Examples | | | | | |
|---|---|---|---|---|---|---|
| | 8 | 9 | Comp. 5 | Comp. 6 | Comp. 7 | Comp. 8 |
| Pressure, psia/source of O2 | 14.7(21% O2) | 764.7(50% O2) | 14.7(21% O2) | 764.7(50% O2) | 764.7(50% O2) | 764.7(50% O2) |
| Conversion, % | 1.1 | 4.6 | 0 | 0 | 11 | 19 |
| Isomer distribution, Area % | | | | | | |
| 2,2' dmbba*** ester | 49.1 | 0.8 | 0 | 0 | 0.4 | 0.3 |
| 4,4' dmbba ester | 0.2 | 6.1 | 0 | 0 | 4.9 | 4.2 |
| Other dmbba ester isomers | 50.7 | 93.1 | 0 | 0 | 94.7 | 95.5 |

*Acetate
**pentanedione
***dimethylbibenzoic acid

In Comparative Examples 5–8, coupling of methyl benzoate was conducted using catalysts disclosed in U.S. Pat. Nos. 3,895,055 and 4,294,976 to Itatani et al. As can be seen from Comparative Example 5, no conversion of methyl benzoate was achieved at atmospheric pressure even at a reaction temperature of 150° C. In contrast, considerable conversion of methyl benzoate to biaromatic compound was achieved in Example 8 according to the present invention, even though the reaction temperature was much lower, at 65° C. Another important advantage of the instant invention is that at elevated pressures conversion or coupling rate of methyl benzoate is unexpectedly higher at 65° C. than the estimated conversion of methyl benzoate at 65° C. using catalysts of Itatani et al. As can be seen from Comparative Example 6, no conversion was achieved using an Itatani et al catalyst at 28° C. To estimate the methyl benzoate coupling rate at 65° C. another experiment using an Itatani et al catalyst at 764.7 psia (50 % O$_2$) was conducted in addition to Comparative Example 7 (100° C. reaction temperature) and Comparative Example 8 (150° C. reaction temperature). The activation energy was calculated from the results of these three experiments. The estimated methyl benzoate coupling rate at 65° C. using an Itatani et al catalyst is only about 4 mmol/hour based on the activation energy data for the reaction. The results of Example 9 show at least twice the conversion rate for methyl benzoate coupling for the catalyst system according to the present invention compared to the catalysts of Itatani et al at the same reaction temperature (65° C.) and at the same pressure (764.7 psia).

What is claimed is:

1. A catalytic system obtained by admixing at least one acid with at least one palladium (II) compound, wherein said acid has a Hammett acidity of less than about –10 and contains a catalytically effective amount of counterions which form weak ligand complexes with palladium (II).

2. The catalytic system according to claim 1, wherein said palladium (II) compound is at least one member selected from the group consisting of palladium triflate and palladium acetate.

3. The catalytic system according to claim 1, wherein said at least one acid is triflic acid.

4. The catalytic system according to claim 1, wherein said at least one acid is a mixture of triflic acid and trifluoroacetic acid.

5. The catalytic system according to claim 4, wherein the amount of said triflic acid is at least 5 % by weight based on the weight of said mixture of triflic acid and trifluoroacetic acid.

6. The catalytic system according to claim 1, wherein the molar ratio of said palladium (II) compound to the amount of said at least one acid or is from about 0.0003:1 to about 10:1.

7. The catalytic system according to claim 3, wherein said palladium (II) compound is at least one member selected from the group consisting of palladium triflate and palladium acetate.

8. The catalytic system according to claim 4, wherein said palladium (II) compound is at least one member selected from the group consisting of palladium triflate and palladium acetate.

9. The catalytic system according to claim 1, wherein said counterions which form weak ligand complexes with palladium (II) are selected from the group consisting of triflate, fluorosulfonate, trifluoroacetate, acetate, acetyl acetonate, bis(trifluoromethylsulfonyl)imide, perfluorotetraphenyl borate, and tetrakis[3,5-bis(trifluoromethyl)phenyl]borate.

10. The catalytic system according to claim 1, wherein said at least one acid has a Hammett acidity of about –14.

11. A method for making 4,4'-substituted biphenyl isomers of the formula

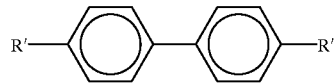

wherein R' is selected from the group consisting of alkyl, carboxyl and carboxylic ester groups, said method comprising homo coupling of a compound selected from the group consisting of alkylbenzenes, benzoic acid and alkylbenzoates in the presence of a catalytic system as defined in claim 1.

12. A method for producing biaryl compounds comprising:
admixing at least one monoaryl compound with a strong acid or a mixture of acids and at least one palladium (II) compound; and subjecting said at least one monoaryl compound to a coupling reaction, wherein said strong acid or said mixture of acids has a Hammett acidity of less than about –10 and contains a catalytically effective amount of counterions which form weak ligand complexes with palladium (II).

13. The method as claimed in claim 12, wherein said monoaryl compound is of the formula:

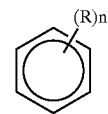

wherein n is an integer from 0 to 5, and
R is the same or different and is selected from alkyl, alkoxy, aryloxy, hydroxy, amino, carboxyl, nitro, nitroso, cyano, amido, hydroxyamino, carboxylic ester, sulfo, and sulfate groups.

14. The method as claimed in claim 12, wherein the molar ratio of said strong acid or said mixture of acids to said monoaryl compound is from about 0.005:1 to about 3:1.

15. The method as claimed in claim 12, wherein said strong acid is triflic acid.

16. The method as claimed in claim 12, wherein said mixture of acids is a mixture of triflic acid and trifluoroacetic acid.

17. The method as claimed in claim 16, wherein the amount of said triflic acid is at least 5% by weight based on the weight of said mixture of acids.

18. The method as claimed in claim 12, wherein said strong acid or said mixture of acids is present in catalytic amounts.

19. The method as claimed in claim 12, wherein said coupling reaction is conducted at a temperature of from about −20° C. to about 150° C.

20. The method as claimed in claim 19, wherein said coupling reaction is conducted at a temperature of from about 0° C. to about 75° C.

21. The method as claimed in claim 12, wherein a catalytic Pd (II) compound amount of used.

22. The method as claimed in claim 21, wherein the amount of Pd (II) compound used is from about 0.001 mole to about 0.1 mole per mole of monoaryl compound.

23. The method as claimed in claim 12, wherein the Pd (II) compound is palladium triflate or palladium acetate.

24. The method as claimed in claim 12, wherein at least two different monoaryl compounds are used in said coupling reaction.

25. The method as claimed in claim 12, wherein said at least one monoaryl compound is a monosubstituted benzene.

26. The method as claimed in claim 25, wherein said monosubstituted benzene is toluene.

27. The method as claimed in claim 26, wherein said biaryl compound comprises at least about 14% on a molar basis of 4,4'-isomer, based upon the total weight of the reaction products.

28. The method as claimed in claim 26, wherein the molar ratio of said strong acid or said mixture of acids to monoaryl compound is from about 0.25:1 to about 2:1.

29. The method as claimed in claim 26, wherein said coupling reaction is conducted at a temperature of from about 0° C. to about 50° C.

30. The method as claimed in claim 25, wherein said monosubstituted benzene is benzoic acid.

31. The method as claimed in claim 25, wherein said monosubstituted benzene is methyl benzoate.

32. The method as claimed in claim 31, wherein said coupling reaction is conducted at a temperature of from about 20° C. to about 75° C.

33. The method as claimed in claim 30, wherein the molar ratio of said strong acid or said mixture of acids to said benzoic acid is from about 0.01:1 to about 0.05:1.

34. The method as claimed in claim 31, wherein the molar ratio of said strong acid or said mixture of acids to said methyl benzoate is from about 0.01:1 to about 0.05:1.

35. The method as claimed in claim 12, wherein said strong acid or said mixture of acids has a Hammett acidity of about −14.

36. A catalytic system obtained by admixing triflic acid with at least one palladium (II) compound.

37. The catalytic system according to claim 36, wherein said palladium (II) compound is at least one member selected from the group consisting of palladium triflate and palladium acetate.

38. The catalytic system according to claim 36, wherein the molar ratio of said palladium (II) compound to the triflic acid is from about 0.0003:1 to about 10:1.

39. The catalytic system according to claim 36 wherein at least one other acid is further admixed with said triflic acid and said at least one palladium (II) compound and wherein the resulting mixture of acids has a Hammett acidity of less than about −10 and contains a catalytically effective amount of counterions which form weak ligand complexes with palladium (II).

40. The catalytic system according to claim 39, wherein said other acid is trifluoroacetic acid.

41. The catalytic system according to claim 40, wherein the amount of said triflic acid is from 5% to 99% by weight based on the amount of said triflic and trifluoroacetic acids.

42. A method for making 4,4'-substituted biphenyl isomers of the formula:

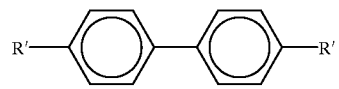

wherein R' is selected from the group consisting of alky, carboxyl and carboxylic ester groups, said method comprising homocoupling of a compound selected from the group consisting of alkylbenzenes, benzoic acid and alkylbenzoates in the presence of a catalytic system as defined in claim 36.

43. A method for producing at least one biaryl compound comprising admixing at least one monoaryl compound with triflic acid and at least one Pd (II) compound, and subjecting said at least one monoaryl compound to a coupling reaction thus producing at least one biaryl compound.

44. The method as claimed in claim 43, wherein said monoaryl compound is of the formula:

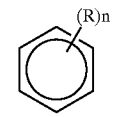

wherein n is an integer from 0 to 5, and
R is the same or different and is selected from alkyl, alkoxy, aryloxy, hydroxy, amino, carboxyl, nitro, nitroso, cyano, amino, hydroxyamino, carboxylic, ether, sulfo, and sulfate groups.

45. The method as claimed in claim 43, wherein the molar ratio of triflic acid to said monoaryl compound is from about 0.005:1 to about 3:1.

46. The method as claimed in claim 43, wherein triflic acid is present in catalytic amounts.

47. The method as claimed in claim 43, wherein said coupling reaction is conducted at a temperature of from about −20° C. to about 150° C.

48. The method as claimed in claim 47, wherein said coupling reaction is conducted at a temperature of from about 0° C. to about 75° C.

49. The method as claimed in claim 43, wherein a catalytic Pd (II) compound amount of used.

50. The method as claimed in claim 43, wherein the amount of Pd (II) compound used is from about 0.001 mole to about 0.1 mole per mole of monoaryl compound.

51. The method as claimed in claim 43, wherein said at least one Pd (II) compound is palladium triflate or palladium acetate.

52. The method as claimed in claim 43, wherein at least two different monoaryl compounds are used in said coupling reaction.

53. The method as claimed in claim 43, wherein said at least one monoaryl compound is a monosubstituted benzene.

54. The method as claimed in claim 53, wherein said monosubstituted benzene is toluene.

55. The method as claimed in claim 54, wherein said biaryl compound comprises at least about 14% on a molar basis of 4,4'-isomer, based upon the total weight of the reaction products.

56. The method as claimed in claim 53, wherein said monosubstituted benzene is benzoic acid.

57. The method as claimed in claim 53, wherein said monosubstituted benzene is methyl benzoate.

58. A catalytic system comprising a combination of a strong acid or a mixture of acids with:
(a) a Pd (II) compound, or
(b) the reaction products or a complex of said Pd(II) compound and said strong acid or said mixture of acids, or
(c) mixtures of (a) and (b);
wherein said strong acid or said mixture of acids has a Hammett acidity of less than about −10 and contains a predominant amount of counterions which form weak ligand complexes with palladium (II).

59. A method for producing at least one biaryl compound comprising:
subjecting at least one monoaryl compound to a coupling reaction thus producing at least one biaryl compound, wherein said coupling takes place in the presence of a combination of a strong acid or a mixture of acids with:
(a) a Pd (II) compound, or
(b) the reaction products or a complex of said Pd (II) compound and said strong acid or mixture of acids, or
(c) mixtures of (a) and (b);
wherein said strong acid or said mixture of acids has a Hammett acidity of less than about −10 and contains a catalytically effective amount of counterions which form weak ligand complexes with palladium (II).

60. A method for producing at least one biaryl compound comprising:
subjecting at least one monoaryl compound to a coupling reaction thus producing at least one biaryl compound, wherein said coupling takes place in the presence of a combination of triflic acid with:
(a) a Pd (II) compound, or
(b) the reaction products or a complex of said Pd (II) compound and said triflic acid, or
(c) mixtures of (a) and (b).

61. A catalytic system according to claim 58 comprising a combination of triflic acid:
(a) a Pd(II) compound, or
(b) the reaction products or a complex of said Pd (II) compound and said triflic acid, or
(c) mixtures of (a) and (b).

62. A catalytic system according to claim 1 obtained by admixing a strong acid or a mixture of acids with at least one palladium (II) compound, wherein the strong acid or the mixture of acids has a Hammett acidity of less than about −10 and contains a catalytically effective amount of counterions that form weak ligand complexes with palladium (II) ion.

63. A catalytic system according to claim 62 wherein the molar ratio of palladium (II) compound to the strong acid or mixture of acids is is the range from about 0.0003:1 to about 10:1.

64. A catalytic system according to claim 63 wherein the strong acid or mixture of acids has a Hammett acidity of less than −14.

65. A catalytic system according to claim 63 wherein the molar ratio of palladium (II) compound to the strong acid or mixture of acids is in the range from about 0.005:1 to about 5:1.

66. A catalytic system according to claim 63 wherein the counterions which form weak ligand complexes with palladium (II) ion are selected from the group consisting of triflate, trifluoroacetate, fluorosulfonate, acetate, acetyl acetonate, bis(trifluoromethylsulfonyl)imide, perfluorotetraphenyl borate and tetrakis[3,5-bis(trifluoromethyl)phenyl] borate.

67. A catalytic system according to claim 63 obtained by admixing palladium triflate, palladium acetate, palladium acetylacetonate or a mixture thereof, and triflic acid, fluorosulfonic acid, a 1:1 to 1:0.15 mixture of antimony pentafluoride and hydrofluoric acid, a 1:0.2 mixture of fluorosulfonic acid with antimony or tantalum pentafluoride, sulfated zirconia or sulfated titania.

68. A method for producing a compound of the formula (II)

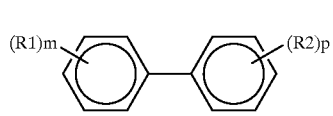

which comprises coupling the same or different compounds of the formula (I)

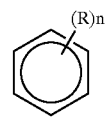

by a coupling reaction in the presence of a catalytic amount of a catalyst system according to claim 63, wherein in formula (I) n is an integer from 0 to 5 and R is the same or different and is alkyl, alkoxy, aryloxy, hydroxy, amino, carboxyl, nitro, nitroso, cyano, amido, hydroxyamino, carboxylic ester, sulfo, sulfate, halogen or another functional group, and in formula (II) m and p can be the same or different and are integers from 0 to 5 which correspond to the respective n's in the compounds of formula (I) and each one of R1 and R2 can be the same or different and correspond to the R's in the compounds of formula (I).

69. A method according to claim 68 wherein the compounds of formula (I) are selected from the group consisting of benzene, toluene, dimethylbenzene, trimethylbenzene, ethylbenzene, isopropylbenzene, xylene, diethylbenzene, diisopropylbenzene, benzoic acid, methyl benzoate, benzonitrile, benzophenone, nitrobenzene, nitrotoluene, anisole, ethoxybenzene, diethoxybenzene, ethoxytoluene, phenol, phenyl acetate and phenyl hexanoate.

70. A method according to claim 68 wherein R is alkyl, alkoxy, aryloxy, hydroxy, amino, carboxyl, nitro, nitroso, cyano, amido, hydroxyamino, carboxylic ester, sulfo or sulfate.

71. A method according to claim 68 wherein n is an integer from 0 to 2 and R is a $C_1$ to $C_4$ alkyl group, a carboxylic acid group or a carboxylic ester group.

72. A method according to claim 71 wherein toluene, benzoic acid or methyl benzoate is coupled.

73. A method according to claim 72 wherein the coupling reaction is carried out in the presence of a catalytic system obtained by admixing triflic acid with palladium triflate.

74. A method according to claim 68 wherein between about 0.005 mole and about 3 moles of the strong acid or the mixture of acids and from about 0.001 mole to about 0.1 mole of palladium (II) compound are used per mole of compound of formula (I).

75. A method according to claim 74 wherein the reaction is carried out at a temperature in the range from about −78° C. to about 200° C. and a pressure in the range from about 14 psia to about 2000 psia.

76. A method according to claim 71 wherein from about 0.25 mole to about 2 moles of the strong acid or the mixture of acids and from about 0.001 mole to about 0.1 mole of palladium (II) compound are used per mole of compound of formula (I).

77. A method according to claim 76 wherein the reaction is carried out at a temperature in the range from about −20° C. to about 150° C. and a pressure which is at least about 14 psia but less than about 1000 psia.

78. A method according to claim 77 wherein the reaction is carried out at a temperature between 0° C. and 50° C.

79. A method according to claim 70 wherein the reaction is carried out at a temperature between 0° C. and 50° C.

* * * * *